United States Patent
Roseman et al.

(10) Patent No.: US 9,682,073 B2
(45) Date of Patent: Jun. 20, 2017

(54) PRE-FRONTAL CORTEX PROCESSING DISORDER GAIT AND LIMB IMPAIRMENTS TREATMENT

(71) Applicant: Gilrose Pharmaceuticals, LLC, White Plains, NY (US)

(72) Inventors: Bruce Roseman, White Plains, NY (US); Gilla Kaplan, New York, NY (US)

(73) Assignee: GILROSE PHARMACEUTICALS, LLC, White Plains, NY (US)

(*) Notice: Subject to any disclaimer, the term of this patent is extended or adjusted under 35 U.S.C. 154(b) by 0 days.

(21) Appl. No.: 15/075,375

(22) Filed: Mar. 21, 2016

(65) Prior Publication Data
US 2016/0199366 A1 Jul. 14, 2016

Related U.S. Application Data

(60) Continuation-in-part of application No. 14/971,325, filed on Dec. 16, 2015, now Pat. No. 9,408,838, which is a division of application No. 14/793,829, filed on Jul. 8, 2015, now Pat. No. 9,307,942, which is a division of application No. 14/453,014, filed on Aug. 6, 2014, now Pat. No. 9,155,502, which is a continuation-in-part of application No. 14/059,541, (Continued)

(51) Int. Cl.
| A61K 31/454  | (2006.01) |
| A61K 31/4458 | (2006.01) |
| A61K 45/06   | (2006.01) |
| A61B 5/055   | (2006.01) |
| A61B 5/00    | (2006.01) |

(52) U.S. Cl.
CPC ........ *A61K 31/4458* (2013.01); *A61B 5/4803* (2013.01); *A61K 31/454* (2013.01); *A61K 45/06* (2013.01); *A61B 5/055* (2013.01); *A61B 5/4064* (2013.01)

(58) Field of Classification Search
CPC .......................... A61K 31/4458; A61K 31/454
USPC ................................................. 514/277, 317
See application file for complete search history.

(56) References Cited

U.S. PATENT DOCUMENTS

| 5,213,553 A | 5/1993 | Light |
| 6,121,261 A | 9/2000 | Glatt et al. |

(Continued)

FOREIGN PATENT DOCUMENTS

| CA | 2 342 432 A1 | 9/2002 |
| WO | WO 2010/015029 A1 | 2/2010 |

(Continued)

OTHER PUBLICATIONS

Moreau, C. et al. Methylphenidate for gait hypokinesia and freezing in patients with Parkinson's disease undergoing subthalamic stimulation; TheLancet; vol. 11, Jul. 2012; pp. 589-596.

(Continued)

*Primary Examiner* — San-Ming Hui
(74) *Attorney, Agent, or Firm* — Marvin Feldman; Lackenbach Siegel, LLP

(57) ABSTRACT

A methylphenidate, particularly including dextro-threo-methylphenidate, is administered to a subject to treat a speech, gait or limb impairment secondary to a genetically acquired pre-frontal cortex processing disease or disorder, particularly including multiple sclerosis, cerebral palsy, Angelman syndrome, Rett syndrome and Fragile-X syndrome.

21 Claims, 11 Drawing Sheets

Related U.S. Application Data filed on Oct. 22, 2013, now Pat. No. 8,883,815, which is a continuation-in-part of application No. 14/112,065, filed as application No. PCT/US2012/038312 on May 17, 2012, now Pat. No. 9,089,563, application No. 15/075,375, which is a continuation-in-part of application No. 14/736,406, filed on Jun. 11, 2015, now Pat. No. 9,220,712, which is a continuation-in-part of application No. 14/112,065, filed on Dec. 24, 2013, now Pat. No. 9,089,563.

(60) Provisional application No. 61/487,847, filed on May 19, 2011.

(56) References Cited

U.S. PATENT DOCUMENTS

| | | | |
|---|---|---|---|
| 8,426,423 | B2 | 4/2013 | Jordan et al. |
| 8,883,815 | B2 | 11/2014 | Roseman |
| 2004/0092605 | A1 | 5/2004 | Jerussi et al. |
| 2006/0052428 | A1 | 3/2006 | Chez |
| 2006/0161218 | A1 | 7/2006 | Danilov |
| 2009/0048288 | A1 | 2/2009 | Ebert et al. |
| 2011/0178114 | A1 | 7/2011 | Aung-Din |
| 2012/0245201 | A1 | 9/2012 | Markowitz et al. |
| 2013/0035363 | A1 | 2/2013 | Greig et al. |
| 2013/0058915 | A1 | 3/2013 | Greenberg et al. |
| 2014/0296210 | A1 | 10/2014 | Garner et al. |
| 2015/0119767 | A1 | 4/2015 | Mor et al. |
| 2016/0199386 | A1 | 7/2016 | Phipps et al. |

FOREIGN PATENT DOCUMENTS

| | | |
|---|---|---|
| WO | WO2013/020136 A2 | 2/2013 |
| WO | WO2014/037412 A1 | 3/2014 |
| WO | WO2015/069505 A1 | 5/2015 |

OTHER PUBLICATIONS

ISR PCT/US2016/037367 and Written Opinion; dated Sep. 7, 2016.
J.M. Hausdorff et al. Maturation of Gait Dynamics: Stride-to-Stride Variability and its Temporal Organization in Children; American Physiological Society; 199; pp. 1040-1047.
N. Papadopoulos et al. An Investigation of Gait in Children with Attention Deficit Hyperactivity Disorder: a Case Controlled Study; Psychiatry Research 218 (2014); pp. 319-323.
Centers for Disease Control and Prevention; Symptoms and Diagnosis ADHD; Ref: American Psychiatric Association; Diagnostic and Statistical Manual of Mental Disorders, $5^{th}$ Ed., (2013).
Yael Leitner et al.; Gait in Attention Deficit Hyperactivity Disorder Effects of Methylphenidate and Dual Tasking; Journal Neurology (2007); 254; pp. 130-1338.
Reorganization after pre-and perinatal Brain Lesions; Martin Staudt; Journal of Anatomy; 2010; pp. 469-474.
New insights into the pathology of white matter tracts in cerebral palsy . . . ; Schecket al.; Developmental Medicine & Child Neurology; Mar. 2012; pp. 684-695.
Pharmacotherapy of Spasticity in Children with Cerebral Palsy; Verrotti et al; Elsevier, Inc. 2006; pp. 1-6.
Speech and Language Therapy for Children with Cerebral Palsy . . . US National Library of Medicine; Jul. 21, 2006; pp. 1-2.
Intensive Speech and Language Therapy for Older Children . . . Cerebral Palsy . . . ; Pennington et al.; Developmental Medicine & Child Neurology; Apr. 2009; pp. 337-344.
Dopamine Treatement in Children with Cerebral Palsy; Shaare Zedek Medical Center; NIH; May 2011; pp. 1-3.
Perceptual and Articulatory Changes in Speech Production . . . Maria I. Griogs, Ph.D., et al.; J. Med. Speech Language Pathol. 2012; 18(4); pp. 46-53.
Speech Problems Affect More Than one in Two Children With Cerebral Palsy . . . A. Nordberg et al.;Acta Paediatriaca; 2012; pp. 161-166.
Speech, Expressive Language, and Verbal Cognition . . . with Cerebral Palsy in Iceland; Developmental Medicine & Child Neurology; Jul. 2010; Solveig et al.; pp. 74-80.
Oromotor Variability in Children with Mild Spastic Cerebral Palsy . . . ; Journal of Neuroengineering and Rehabilitation; 2010; Chia-Ling Chen, et al.; pp. 1-10.
Oromotor Dysfunction and Communication Impairments in Children with Cerebral Palsy . . . ; Parkes, et al.; Developmental Medicine & Child Neurology; Jun. 2010; pp. 1113-1119.
Long-Term Survival for a Cohort of Adults with Cerebral Palsy; Hemming Ph.D., et al.; Developmental Medicine & Child Neurology; 2006; 48: pp. 90-95.
Development of the FOCUS, a Communication Outcome Measure for Preschool Children; Thomas-Stonell, et al. Developmental Medicine & Child Neurology; Jun. 2009; pp. 47-53.
Language and Motor Speech Skills in Children with Cerebral Palsy; Pirila, et al.; Journal of Communication Disorders 40: (2007); pp. 116-128.
Survival of Individuals with Cerebral Palsy Born in Victoria, Australia . . . ; Reid, et al.; Developmental Medicine & Child Neurology; Oct. 2011; pp. 353-360.
Factors Associated with Motor Speech Control in Children with Spastic Cerebral Palsy; Chia-Ling Chen, et al.; Chang Gung Medical Journal; vol. 33, No. 4; Jul.-Aug. 2010; pp. 415-423.
Intensive Speech and Language Therapy for Older Children with Cerebral Palsy: A Systems Approach; Penning, et al.; Developmental Medicine & Child Neurology; Apr. 2009; pp. 337-344.
Dysarthria Treatment; Chandramita Bora; Apr. 19, 2010; Buzzle; pp. 1-2.
Speech and Language Therapy for Children with CP might Improve their Communication Skills, but More Research is needed; PubMed Health/NIH; John Wiley & Sons, Ltd. pub. Jul. 21, 2003.
NINDS Cerebral Palsy Information Page; NIH National Institute of Neurological Disorders and Stroke . . . Aug. 21, 2013.
The Effect of Methylphenidate on the Verbal Productivity of Children with Cerebral Dysfunction; Ray O. Creager and Catharine Van Riper; J. Speech Hear Res. 1967:10; 623-628.
Methylphenidate for Giggle Incontinence; Amanda K. Berry et all., The Journal of Urology; vol. 182; Issue 4, Supplement; pp. 2028-2032; Oct. 2009.
Methylphenidate for the Treatment of Gait Impairment in Parkinson's Disease; NIH Clinical Trials; pp. 1-5; Oct. 27, 2009.
PCT/US2012/028212 international search report and written opinion, dated Nov. 7, 2012.
PCT Publication WO 2012/158892 A2; published Nov. 22, 2012.
ISR PCT/US2014/060868, dated Mar. 27, 2015.
Written Opinion PCT/2014/060868, dated Mar. 27, 2015.
Pennington et al., Effects of it Takes Two to Talk, the Hanen Program for Parents of Preschool Children with CP . . . ; Journal of Speech, Language and Hearing Research 52, (5) 1121-1138 (2009).
Effect of Amphetamines of Speech Defects in the Mentally Retarded; Charles H. Fish, MD., MPH, et al. California Medical Association; vol. 96, No. 2, Feb. 1962; pp. 109-111.
Effect of Single Dose Methylphenidate on Walking and Postural . . . Oxford Journals Medicine & Health & Science & Mathematics Journal of Gerontology Series A; vol. 68, Issue 10, pp. 1271-1280 The Biological Sciences and Medical Sciences; Zamir Shorer et al.
Stability and Decline in Gross Motor Function Among Children and youth with Cerebral Palsy . . . , Steven E. Hanna, PhD., Developmental Medicine & Child Neurology, vol. 51, Issue 4, Apr. 2009, pp. 295-302.
Methylphenidate for Cerebral Palsy with Choreoathetois, Willem Boogerd, MD, PhD, ACP, vol. 13, Mar. 21, 2000, pp. 1-2.
Practice Parameter: Pharmacologic Treatment of Spasticity in children . . . M.R. Delgado et al., Neurology 2010, Jan. 26; 74(4); pp. 336-343.
[3 H] Threo-(±)-Methylphenidate Binding to 3,4-Dihydroxphenylethylamine . . . Properties of Ritalinic Acid Esters; Margaret M. Schwere et al. Journal of Neurochemistry, vol. 45, No. 4, 1985, pp. 1062-1070.

(56) References Cited

OTHER PUBLICATIONS

Relative Hydrolytic Rates of Certain Alkyl . . . phenylacetrates; Philip S. Portoghese et al; Journal of Pharmaceutical Science, vol. 50, No. 6, Jun. 1961.
Activity, Activity . . . Approach to Cerebral Palsy; Diane L. Damiano, Physical Therapy, Nov. 2006, vol. 86, No. 11; pp. 1534-1540.
What is Rett Syndrome, National Institute of Neurological Disorders and Stroke, Pub date Nov. 2009 NIH Pub. No. 09-4863; pp. 1-7.
New Methylphenidate Formulations for the Treatment of . . . disorder; Patrick et al.; Expert Opinion on Drug Delivery;pp. 121-143.
Methylphenidate and its Isomers; Heal et al; CNS Drugs 2006; 20 (9); pp. 713-738.
PCT/ISA/224 ; PCT Communication Form, dated Sep. 29, 2016.
PCT/USA/220; PCT transmittal ISR/Written Opinion, dated Sep. 29, 2016.
PCT/ISA/210; PCT Corrected ISR, dated Sep. 29, 2016.
PCT/ISA/237, Dated Sep. 29, 2016.
Demand for Reconsideration and Amendment; 11pp, dated Jan. 31, 2017.
Exhibit A; Pars Compacta, pp. 1-3; Wikipedia.
Exhibit B; Office Action; U.S. Appl. No. 15/075,375; Oct. 5, 2016; 9 pp.
Exhibit C; Methylphenidate for Parkinson Disease Gait Disorders; Lancet Neurology Jun. 1, 2012; Michael S. Okun, MD; pp. 1-4.
Exhibit D; Methylphenidate for Gait Impairment in Parkinson Disease; Abstract; Neurology Journal; Apr. 5, 2011; vol. 76, No. 1256-1262; p. 1.

PRE-FRONTAL CORTEX PROCESSING DISORDER GAIT AND LIMB IMPAIRMENTS TREATMENT

PRIOR RELATED APPLICATIONS

This application is a continuation-in-part application of U.S. application Ser. No. 14/971,325, filed Dec. 16, 2015, which is a divisional application of U.S. application Ser. No. 14/793,829, filed Jul. 8, 2015, now U.S. Pat. No. 9,307,942, which is a divisional application of U.S. application Ser. No. 14/453,014, filed Aug. 6, 2014, now U.S. Pat. No. 9,155,502, which is a continuation-in-part application of U.S. application Ser. No. 14/059,541, filed Oct. 22, 2013, now U.S. Pat. No. 8,883,815, which is a continuation-in-part application of U.S. application Ser. No. 14/112,065, filed Dec. 24, 2013, now U.S. Pat. No. 9,089,563, which is a US 371 National Phase application of PCT/US2012/038312, filed May 17, 2012, which claims priority to U.S. Provisional Application No. 61/487,847, filed May 19, 2011; and this application also claims priority to U.S. application Ser. No. 14/736,406, filed Jun. 11, 2015, now U.S. Pat. No. 9,270,712, which is a continuation-in-part application of U.S. 371 application Ser. No. 14/112,065, filed Dec. 24, 2013, now U.S. Pat. No. 9,089,563;
which applications are incorporated herein in their entireties by reference thereto.

FIELD OF THE INVENTION

This invention relates to a pharmaceutical intervention and method for treating a speech, gait or limb impairment, particularly including an impairment secondary to a disease or disorder. This invention also relates to a pharmaceutical intervention for a subject with motor deficits in the limbs. More specifically, this invention also relates to a pharmaceutical intervention for treating gait, limb and speech impairments secondary to a pre-frontal cortex processing a disease or disorder, particularly wherein there are brain or central nervous system lesions. More specifically, this invention also relates to a pharmaceutical intervention for treating gait or limb abnormalities or impairments resultant from multiple sclerosis, (MS), cerebral palsy (CP), Angelman syndrome (AS), Rett syndrome (RS) and Fragile-X syndrome (FXS).

BACKGROUND AND DISCUSSION OF THE PRIOR ART

Cerebral palsy (CP) is a non-progressive disease or disorder involving irreparably damaged or injured areas of the brain, including connections between the cortex particularly the pre-frontal cortex, and other parts of the brain or central nervous system (CNS) and the muscles in the peripheral nervous system. The National Institute of Neurological Disorders and Stroke (NINDS) of the National Institutes of Health (NIH) defines cerebral palsy as any of a number of neurological disorders that appear in infancy or early childhood and permanently affect body movements and muscle coordination but do not worsen over time, and the NIH makes clear that cerebral palsy cannot be cured.

Infantile cerebral palsy (ICP) refers to a disorder affecting movement. Infantile spastic cerebral palsy refers to ICP with spastic motor defects. Generally, infantile spastic cerebral palsy can be separated into two groups: (1) the symmetric palsies, including the diplegias, which exhibit symmetric involvement on both sides of all four extremities but to a greater degree in the legs, and the paraplegias, in which the lower extremities are equally involved, and (2) the asymmetric palsies which include the hemiplegias, monoplegias, triplegias and quadriplegias. The quadriplegias differ from the diplegias in that all four extremities are more or less irregularly involved often with equal or greater spasticity in the arms.

A most common type of spastic cerebral palsy is spastic diplegia. Most individuals with spastic diplegia exhibit scissors gait. Scissors gait is characterized by adduction and internal rotation at the hip, rigidity and excessive adduction of the leg in swing, flexion at the knee, planton flexion at the ankle and contractions of the spastic muscles. Other cerebral palsy gait impairments include toe down where the toe is pointing down and inward. Such gait impairments result in the toe-to-heel step as opposed to the correct heel-to-toe step. Toe-to-heel step in turn causes considerable pain to the individual. Some individuals may exhibit combinations of such characteristics.

Multiple sclerosis (MS), like cerebral palsy (CP), is a pre-frontal cortex processing disorder, often associated with lesions in the brain or central nervous system (CNS). MS and CP have resultant deficits or impairments in speech, gait or limb. These impairments include, by way of example, dysarthric speech, gait or limb abnormalities such as toe down, foot drop, spasms, ataxia and related fatigue. The present invention contemplates a pharmaceutical intervention for treating a speech, gait or limb impairment secondary to pre-frontal cortex processing disorder, particularly including MS and CP.

Rett syndrome (RS) is a genetically acquired pre-frontal cortex processing disorder having a secondary limb impairment, particularly non-specific hand wringing. Angelman syndrome (AS), like RS, is also a genetically acquired pre-frontal cortex processing disorder having a secondary limb impairment, particularly non-specific arm flapping, as well as gait and speech impairments. The present invention contemplates a pharmaceutical intervention for treating a speech, gait or limb impairment secondary to a genetically acquired pre-frontal processing disorder, particularly including RS and AS.

MS and CP, like RS and AS, may be genetically acquired. The MS, CP, RS and AS secondary gait or limb impairments, however, are often later manifested in the life of the subject. The present invention contemplates the pharmaceutical intervention at the onset of the impairment in a child.

Attempts to treat gait impairments and spasticity include devices such as a therapeutic chair as disclosed in U.S. Pat. No. 4,145,083, issued Mar. 20, 1979 to Urban; transcranial electrode stimulation as disclosed in U.S. Pat. No. 4,844,075, issued Jul. 4, 1989 to Liss; transcranial magnetic stimulation as disclosed in US2011/0270345 A1, published Nov. 3, 2011 to Johnston et al.; neurosurgery as disclosed in U.S. Pat. No. 6,936,049, issued Aug. 30, 2005 to Svadovskiy; botulism toxin as disclosed in U.S. Pat. No. 7,378,389, issued May 27, 2008 to Graham; and combinations of botulism toxins with automated movement therapy as disclosed in US 2008/0279896 A1, published Nov. 13, 2008, to Heinen et al. Heinen et al. discloses pharmaceutical muscle stimulation prior to and in combination with botulism toxin and in further combination with automated movement interventions. Injectable pharmaceuticals, such as interferon derivatives, particularly including Plegridy® (peginterferon beta-1a), are known in the treatment of multiple sclerosis, and such injectables cause debilitating pain. Thalidomide and its analogs are known to treat multiple sclerosis.

Parkinson's disease is a degenerative disorder of the cerebral nervous system effecting specific motor systems that result specifically from the dearth of dopamine generating in the basal ganglia. Parkinson's disease is an idiopathic degenerate disorder that develops usually in individuals 60 years of age or older. A brain scan of an individual with Parkinson's' disease reveals no brain damage, unlike cerebral palsy and multiple sclerosis. Parkinson's disease is characterized by stiffness or rigidity, slow and decreased movements resulting in gait instability and the readily recognizable Parkinson's shuffle. Parkinson's gait rigidity is markedly distinguished from cerebral palsy spasticity. Insofar as Parkinson's disease results from a loss of dopamine, one treatment is the administration of dopamine agonists particularly methylphenidate, as disclosed in *Methylphenidate for the Treatment of Gait Impairment in Parkinson's Disease*; NIH Clinical Trials, pp 1-5; Oct. 27, 2009; and dopamine transporter inhibitors, as disclosed in U.S. Pat. No. 8,258,305, issued Sep. 4, 2012 to Hauske.

The art desires a pharmaceutical intervention or treatment for a pre-frontal cortex processing disorder resultant speech, gait or limb impairment that does not require mechanical, electro-mechanical, invasive and toxic interventions.

The art also desires a treatment as aforesaid including a pharmaceutical intervention and method for treating a speech, gait or limb impairment secondary to a genetically acquired pre-frontal cortex processing disorder.

The art desires a pharmaceutical intervention as aforesaid wherein the impairment is diminished, and the diminishment in the impairment persists and continues over time, even when the pharmaceutical intervention is no longer efficaciously present.

The art also desires a pharmaceutical intervention as aforesaid as well as a combination of pharmaceuticals, for the simultaneous treatment of a speech, gait or limb impairment secondary to MS, CP, AS, RS and FXS.

The art also desires a pharmaceutical intervention for a speech, gait or limb impairment as aforesaid that is readily administered, efficacious and safe, with ready and persistent diminishment of the impairment.

The present invention provides a solution to the aforesaid needs.

SUMMARY OF THE INVENTION

The invention, in one principal aspect, is a pharmaceutical intervention for treating a speech, gait or limb impairment secondary to a pre-frontal cortex processing disorder in a subject. The pharmaceutical intervention is a psychostimulant having mood-elevating or antidepressant activity, particularly an NDRI. In a preferred aspect, the pharmaceutical intervention is a methylphenidate, and most preferably dextro-threo-methylphenidate.

The invention is a pharmaceutical intervention as aforesaid for genetically acquired disorders, particularly including Angelman syndrome (AS) and Rett syndrome (RS).

The invention is a pharmaceutical intervention as aforesaid for generally non-degenerative or non-progressive disorders particularly including cerebral palsy (CP) and Angelman syndrome (AS).

The invention is a pharmaceutical intervention as aforesaid which disorder was acquired genetically, in utero, at birth or shortly after birth, and the impairment later manifested. Genetically acquired and in utero acquired disorders, particularly including cerebral palsy (CP), Angelman syndrome (AS) and Rett syndrome RS), are within the contemplation of the present invention.

The impairments treated by the pharmaceutical intervention of the present invention include, by way of specific examples, dysarthric speech, limb spasms, toe or foot drop, non-specific hand wringing, and non-specific arm flapping.

Without wishing to be bound by any theory or mechanism, it is believed that the administered NDRI, particularly including a methylphenidate, and more particularly dextro-threo-methylphenidate, provides or restores neural pathways extending from the prefrontal cortex so as to provide improved processing management and control with consequential diminishment in the speech, gait or limb impairment.

Without wishing to be bound by any theory or mechanism, it is also believed that the methylphenidates administered pursuant to the present invention may affect or restore neural pathways between upper motor neural lesion areas of the brain and the spine.

BRIEF DESCRIPTION OF THE DRAWINGS

FIG. 2 demonstrates that the GMFCS level number after a regimen of the pharmacological intervention of the present invention is at least one level number less than before the regimen.

DESCRIPTION OF THE INVENTION

Figure 1:
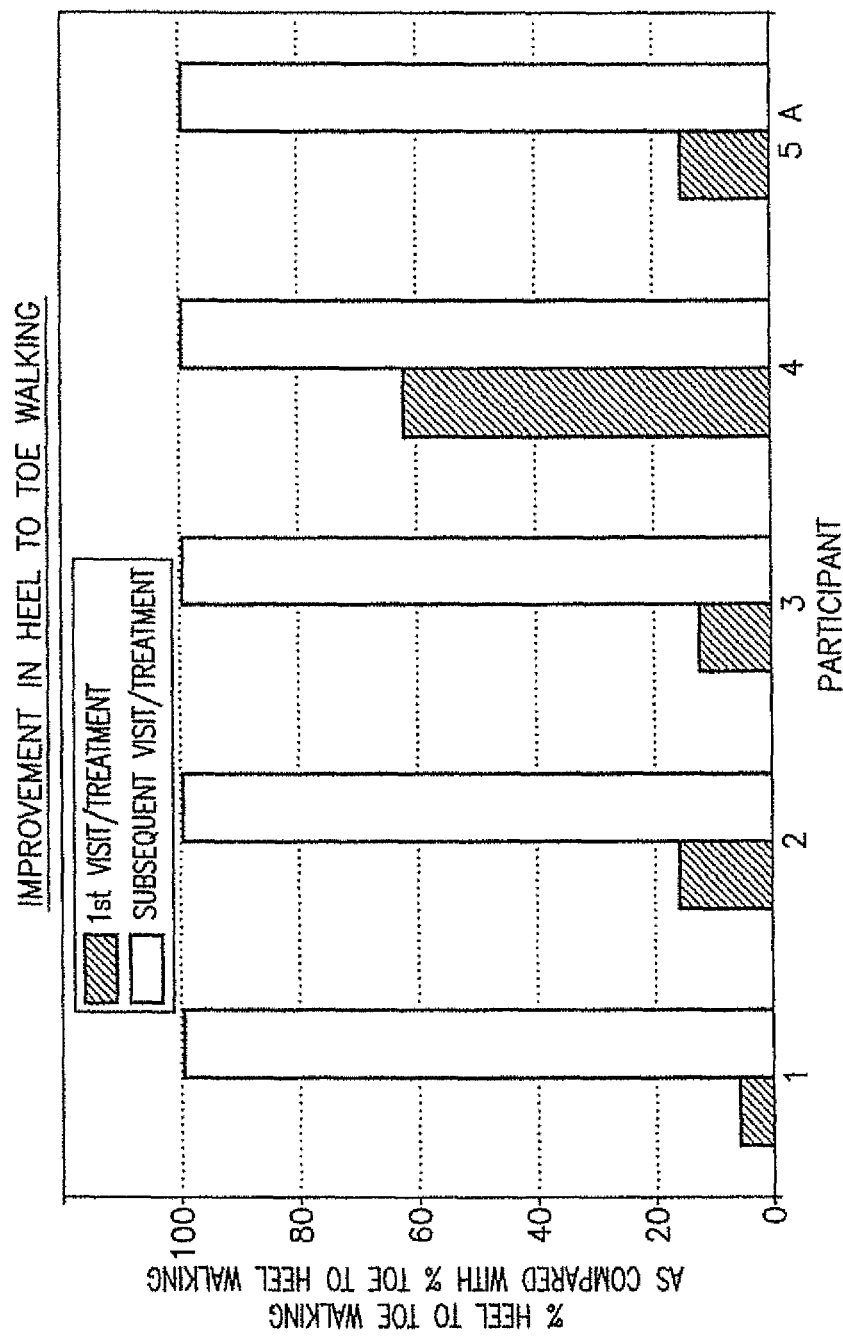
FIG. 1 shows the % heel-toe-toe as compared to % toe-to-heel step gait at the initial administration of a pharmacological intervention of the present invention and at the time of a subsequent administration of a pharmacological intervention pursuant to the present invention for Participants 1-5A.

The term "subject" as used hereinbefore and hereinafter means a human or other mammal, and includes a patient, or a participant in a study or clinical trial.

The term "therapeutically effective dose" or "therapeutically effective dosage" as used hereinbefore and hereinafter means an amount of the administered substance that is sufficient to provide a diminishment of the impairment.

The term "psychostimulant" as used hereinbefore and hereinafter is broadly defined to include an NDRI having antidepressant or mood-elevating properties, and as further discussed hereinafter.

The terms "MPH" and "MPD" as used hereinbefore and hereinafter refer to racemic methylphenidate.

The term "genetically acquired" or "acquired genetically", as used hereinbefore and hereinafter includes genetically inherited defects and mutations, and chromosomal defects, as well as genetically transmitted or pre-dispositioned disorders.

The term or acronym "GMFCS" means Gross Motor Function Classification System. The gross motor skills (e.g. sitting and walking) of children and young people with cerebral palsy can be categorized into 5 different levels using a tool called the Gross Motor Function Classification System (GMFCS). The GMFCS levels are: Level 1—walks without limitations; Level II—walks with limitations. Limitations include walking long distances and balancing, but not as able as Level I to run or jump; may require use of mobility devices when first learning to walk, usually prior to age 4; and may rely on wheeled mobility equipment when outside of home for traveling long distances; Level III—walk with adaptive equipment assistance. Requires hand-held mobility assistance to walk indoors, while utilizing wheeled mobility outdoors in the community and at school; can sit on own or with limited external support; and has some independence in standing transfers; Level IV—self-mobility with use of powered mobility assistance. Usually supported when sitting; self-mobility is limited; and likely to be transported in manual wheelchair or powered mobility; and Level V—severe head and trunk control limitations. Requires extensive use of assisted technology and physical assistance; and transported in a manual wheelchair, unless self-mobility can be achieved by learning to operate a powered wheelchair.

The terms "visit", "examination" or "visit/examination" refer to an examination of the Participant by a pediatric neurologist.

The present invention includes the administration of a therapeutically effective dose of one or more of a broad range of NDRIs or dopamine agonists including a methylphenidate, particularly including dextro-threo-methylphenidate, (Focalin®), and the non linear lower alkyl phenidates, particularly including isopropyiphenidate.

The present invention treats subjects, particularly children, diagnosed with cerebral palsy having secondary disorders including both a gait impairment and a speech impairment. The treatment of speech impairment secondary to cerebral palsy is disclosed in co-pending application Ser. No. 14/453,014, filed Aug. 6, 2014, and in parent application Ser. No. 14/059,541, filed Oct. 22, 2013, now U.S. Pat. No. 8,883,815, which references are incorporated herein in their entireties by reference thereto.

The present invention contemplates a combination of two medicaments, a first medicament that efficaciously treats a certain disease or disorder but has an adverse side effect, namely a gait or limb abnormality or impairment and/or speech impairment, and a second medicament namely a psychostimulant having mood elevating or anti-depressant properties, particularly including a methylphenidate, that diminishes the gait, limb or speech impairment.

The art discloses that thalidomide can be used in the treatment of ALS, as disclosed in US Pub. 2005/0182097, published Aug. 18, 2005 to Zeldis et al. The present pharmaceutical intervention may likewise be used to treat speech, limb or gait impairments resultant from or in combination with the thalidomide or an analog treatment of the genetically acquired ALS and other genetically acquired disorders.

It is also within the contemplation of the present invention to combine or co-administer thalidomide or a thalidomide analog, or Abraxane® known to have gait abnormalities side effects with the psychostimulant of the present invention, particularly methylphenidate, and more particularly dextro-threo-methylphenidate, to efficaciously treat the disorder while diminishing or precluding the gait, limb and speech impairments incident to a thalidomide regimen, Abraxane® regimen or to the disease or disorder. Limb impairments incident to seizures, particularly epileptic seizures, are also within the contemplation of the present invention.

It has been surprisingly found that the pharmaceutical intervention and method of the present invention diminishes the aforesaid impairments, which diminishment in impairments and pain persists even when the pharmaceutical intervention is no longer efficaciously present.

EXAMPLES

Participant 1

Participant 1 is a male and was 8 years old at the time of the first pharmacological intervention pursuant to the present invention. Participant 1 had delayed speech and language. Participant 1 was diagnosed as having spastic dipligea, bilateral contractures at the hips. Participant 1 wore leg braces prior to the pharmacological intervention, and the braces were removed in the initial visit. Prior to the pharmacological intervention of the present invention, Participant 1 was treated with Botox injections, oral baclofen and orthotics. The parents of Participant 1 stopped all such treatments because they did not observe any improvement in gait.

Figure 2:
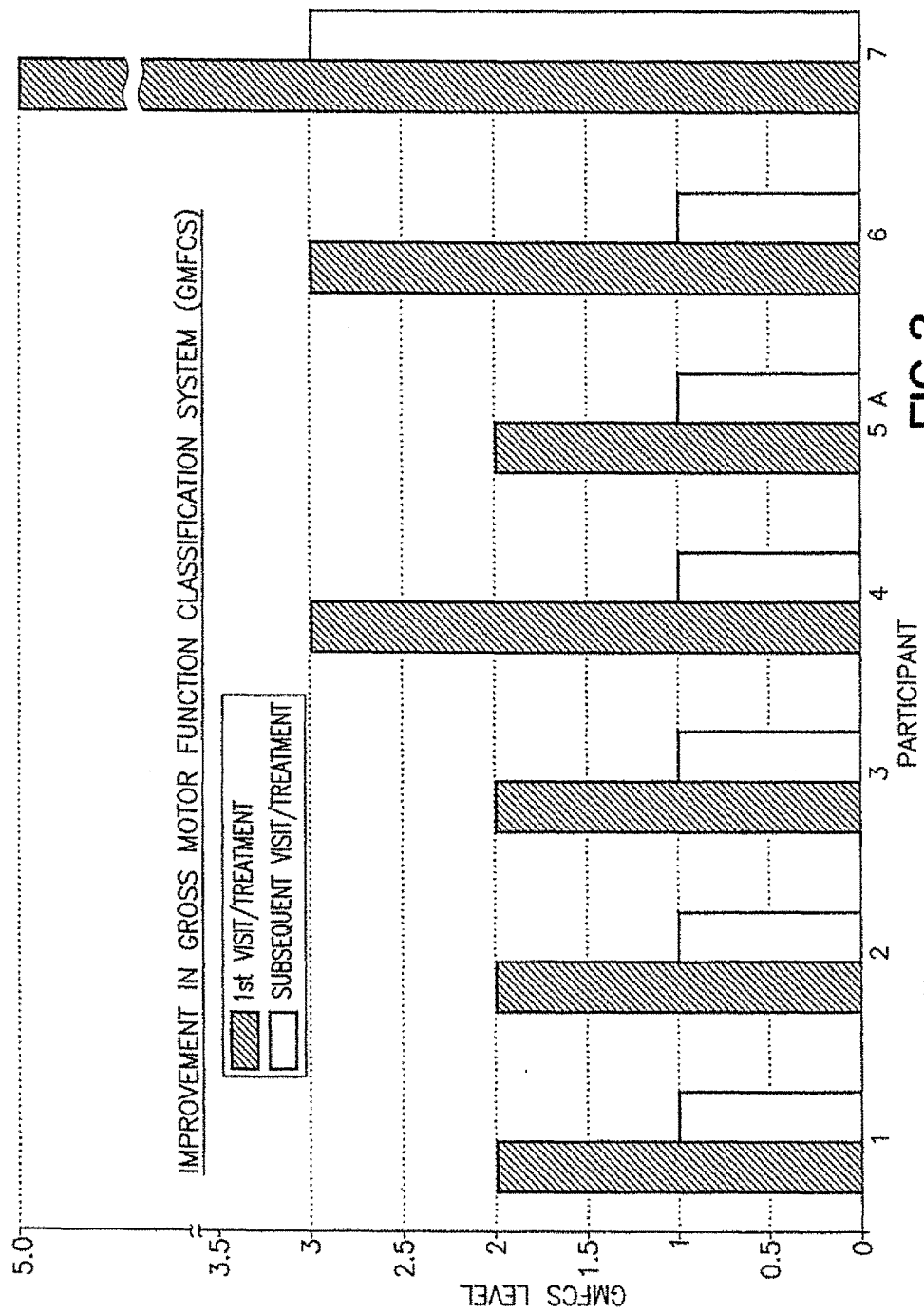
FIG. 2 shows the GMFCS level at the initial time prior to and after a pharmacological regimen of the present invention for Participants 1-7.

The initial pharmacological intervention was 2 cc (10 mg) of Quillivant XR®, and one month later was replaced with 5 mg of racemic methylphenidate (MPD)/day. FIGS. 1-2 for Participant 1 shows the improvement in gait after about 45 minutes at the initial visit, and after daily treatments of 5 mg methylphenidate/day.

Participant 2

Participant 2 is a female and was 15 years old at the time of the initial pharmacological intervention pursuant to the present invention. Participant 2 did not start to walk until 18 months of age, and had significantly delayed speech and language development. She was not speaking in sentences until she was 5 years of age.

Participant 2 was diagnosed with spastic dipligea and painful gait. Participant 2's weight increased because of the avoidance of walking to preclude the concomitant pain.

After about one year of daily methylphenidate administrations, Participant 2 could walk on a flat surface and up and down stairs with flexibility, even when the methylphenidate is no longer efficaciously present in the body.

Participant 2 reports she is pain free, has entered the school talent show and exhibits a 15 minute dance routine performed at school.

Participant 3

Participant 3 is a female and was about 15 years of age at the first pharmacological intervention pursuant to the present invention.

Participant 3 had an initial diagnosis of cerebral palsy, epileptic encephalopathy, global development delay, left hemiplegia and spastic dipligea, left greater than right. At the initial visit, Participant 3 was physically examined and found to have a limited amount of receptive and expressive language, with the left side of the body much smaller than the right side, left hemiplegia, contractions of the left elbow, and unable to open left hand, with the fingers and thumb kept in fisted position. Participant 3 loses balance and falls if not assisted when rising from a chair. When walking on a flat surface, she keeps her left elbow at 90 degrees, left hand remains in a fisted position, toe-to-heel gait, bilateral left greater than right. And to avoid tripping over her left foot, she keeps her left foot in extension securing her left leg as far away from her trunk in order for her left foot to have enough clearance to avoid first hitting the ground with he extremities.

A 400 mg/day Gabapentin regimen was prescribed. After 2 months, there was a 5 mg MPD initial administration. This was followed by 5 mg MPD/day for a period of 11 months, FIGS. 1-2 show Participant 3 gait improvement at the initial intervention, and after the 11 months of the foregoing regimen.

Participant 3 reports playing sports, even when the MPD is no longer efficaciously present.

Participant 4

Participant 4 is a female, and was about 19 years of age at the time of first pharmacological intervention of the present invention. Participant 4 was born prematurely at 24 weeks. Participant 4 had a twin. The twin died on day one. Participant 4 suffered hypoxia at birth. Participant 4 first began to walk and talk well over 2 years of age. Participant 4 was diagnosed with cerebral palsy and global developmental delay, Hashimoto's thyroiditis, epilepsy, scoliosis and spastic dipligea. An MRI of the brain revealed periventricular leukomalacia. The initial visit revealed that Participant 4 walks with a crouched gait, flexed at the hips and knees, lateral fixed contractions, and obligated toe to heel gait with pain when walking and calf muscular pain when not walking. Medication administered long prior to and during the pharmacological intervention of the present invention included the anti-seizure medicament oxcarbazepine (Trilepal®). Oxcarbazepine (Trilepal®) is reported to cause gait abnormalities as a side effect.

The improvements in gait and step after the two weeks of daily MPD administration are shown in Table I.

TABLE I

| Heel-to-Toe/Toe-to-Heel (Sec./Sec.) | Stairs Holding to Railings Up (Sec./Sec.) | Stairs Holding Railings Down (Sec./Sec.) |
| --- | --- | --- |
| Initial 9.38/15 | Initial 7.4/59 | Initial 12.81/59 |
| After 2 Weeks 15/15 | After 2 Weeks 0/60 | After 2 Weeks 0/60 |

Participant 4 Example demonstrates improvements in gait including step with co-administration of an anti-seizure medicament having a gait impairment side effect.

It is within the contemplation of the present invention to combine the present pharmacological intervention with a medicament for treating a disease or disorder but with gait abnormality or impairment side effects, whereby the disease or disorder is treated and the impairment side effects are precluded or diminished, particularly as demonstrated in the Participant 4 Example.

Participant 5A

Participant 5A is a female 13 years of age at the time of the first examination pursuant to the present invention. Participant 5A has an identical twin; hereinafter referred to as Participant 5B. Participants 5A and 5B were born to a drug addicted alcoholic woman and were diagnosed with speech and gait impairments secondary to cerebral palsy. Participant 5A had a speech-language disorder and spastic diplegia, Participant 5A had to direct both legs in extension to avoid tripping over her own feet because she was unable to flex and extend at the ankle joint to move her feet, resulting from the spastic dipligea.

At the first visit/treatment, 5 mg of methylphenidate was administered to Patent 5A. Prior to the administration, Participant 5A had no heel-to-toe functionality. After administration, Participant 5A had generally 43% heel-to-toe walking time in both feet in walking and up and down stairs. See FIG. 1. Participant 5A reported no pain after walking.

Figure 3:
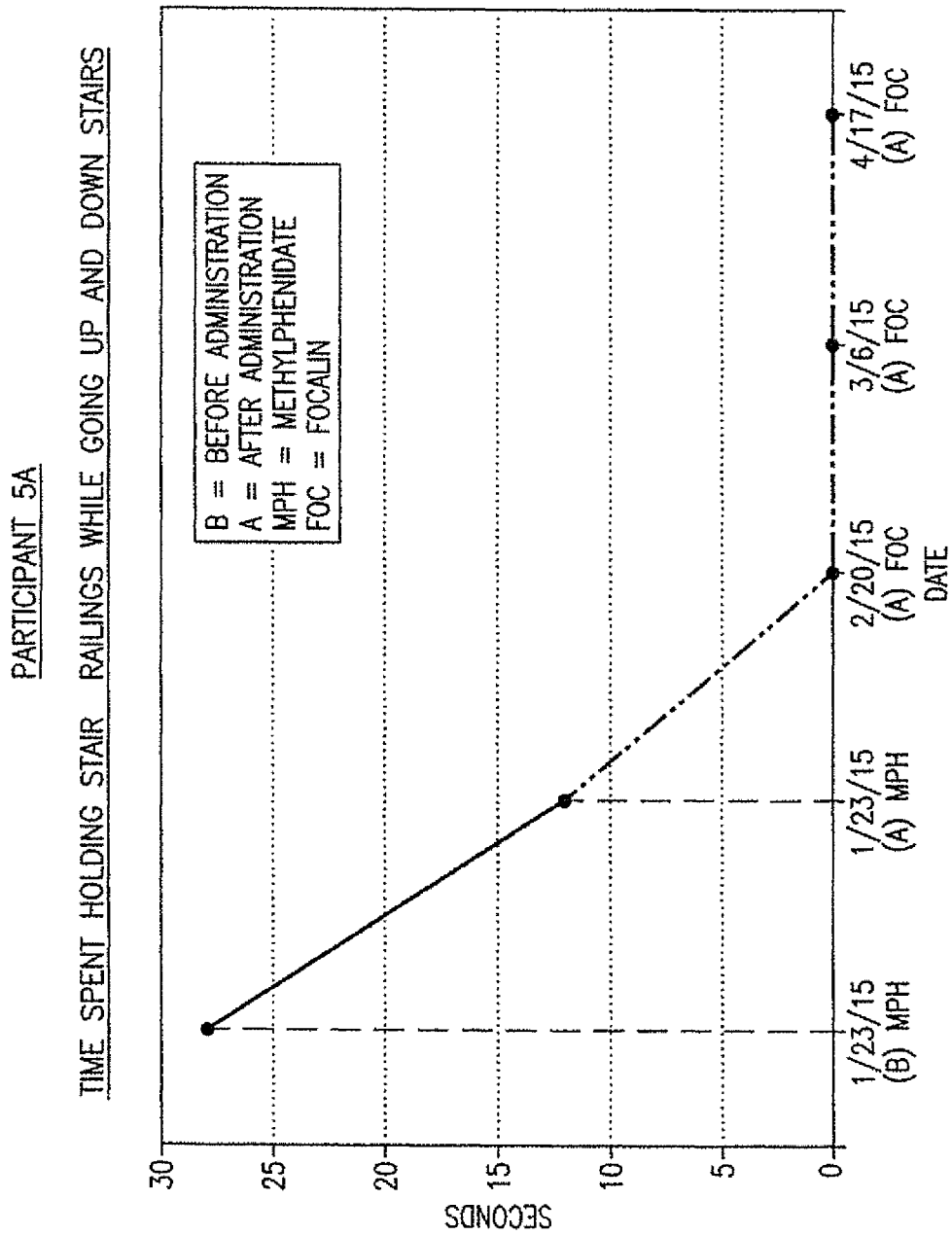
FIG. 3 is a graph of the time spent holding stair railings while going up and down stairs in an initial visit/examination before and after pharmaceutical intervention, and in subsequent visits/examinations for Participant 5A. The solid line is the within the hour measurements at a specific visit/examination, and the broken line is the timeframe between visits/examinations.
Figure 4:
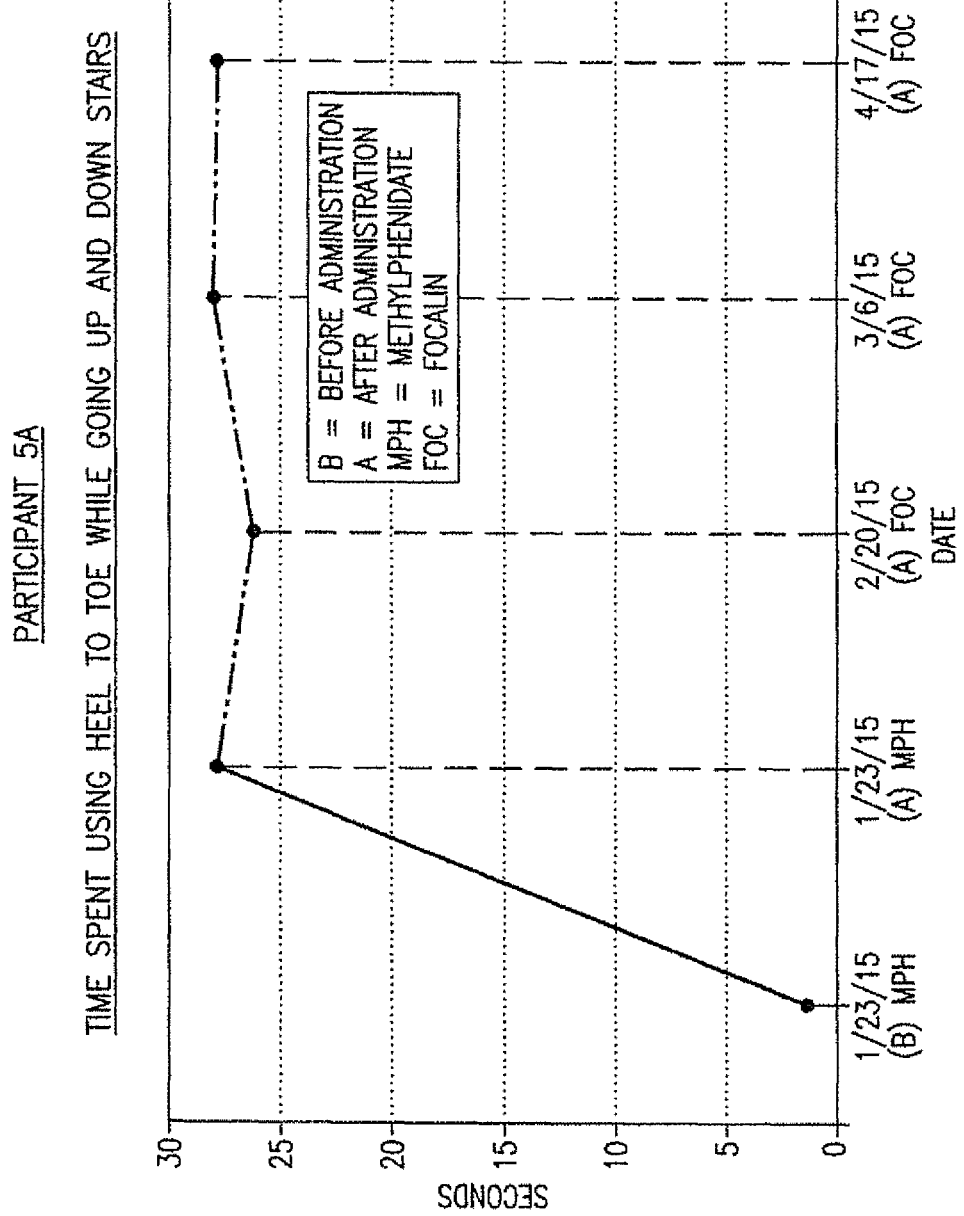
FIG. 4 is a graph of the time spent in a 30 second timeframe in heel-to-toe walking while going up and down stairs at an initial visit/examination before and after the initial pharmaceutical intervention, and in subsequent visits/examinations for Participant 5A. The solid line is the within the hour measurements at a specific visit/examination, and the broken line is the timeframe between visits/examinations.
Figure 5:
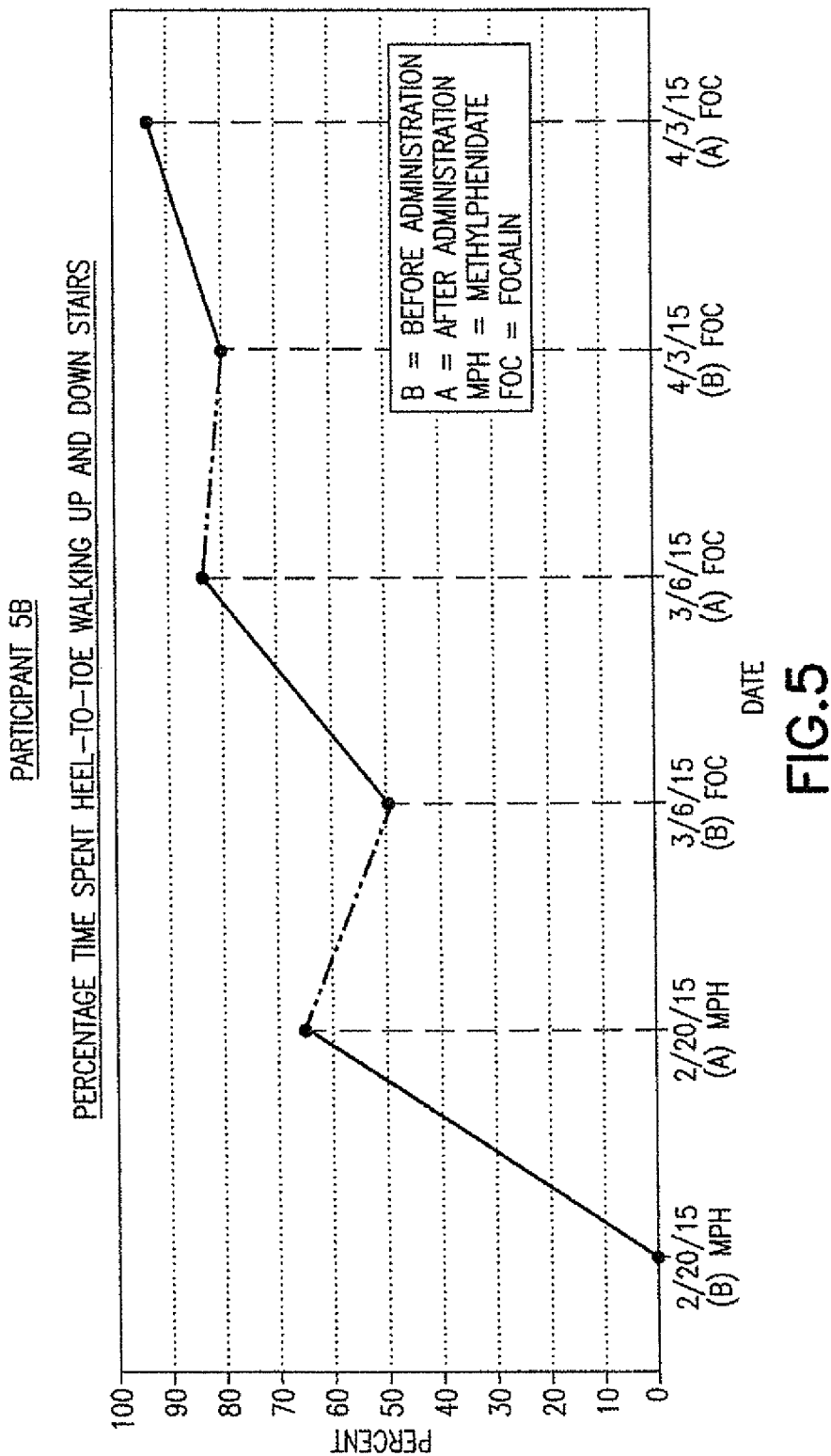
FIG. 5 is a graph of the percentage time in correct heel-to-toe gait when walking up and down stairs in an initial visit/examination before and after the initial pharmaceutical intervention and in subsequent visits/examinations for Participant 5B.

Referring specifically to FIGS. 3 and 5, there is shown the dramatic improvement in heel-to-toe steps in traversing stairs, for Participant 5A, particularly with a Focalin® regimen in lieu of a racemic methylphenidate regimen.

Participant 5B

Participant 5B is the identical twin of Participant 5A. Participant 5B was diagnosed with severe speech impairment secondary to cerebral palsy. Participant 5B, unlike her twin sister, Participant 5A, did not have quite as severe gait impairment. Participant 5B, however, could not keep her foot straight and had to hold onto railings ascending or descending stairs.

In the first examination, because the speech impairment was so severe, Participant 5B was diagnosed as mentally retarded. There was no volitional speech. Participant 5B could not read or comprehend at a second grade level.

In the second examination, a regimen of 5 mg MPD/day was prescribed, to be taken before school.

At the beginning of the third examination, about one month after the second examination, 5 mg MPD was administered. After 40 minutes, Participant 5B had spontaneous speech of 4-6 words, as opposed to the 2-3 word capability in the first examination. Participant 56 comprehended at a second grade level. A revised regimen of 10 mg MPD/day before school was prescribed.

A fourth examination occurred approximately one month after the third examination. Participant 56 was administered 10 mg Focalin®. After 40 minutes, Participant 5B was able to keep her foot straight in walking and did not feel like she was going to fall.

Participant 5B had a regimen of 10 mg/day Focalin® for the next 14 days. A fifth examination was undertaken after the 14 days of Focalin®. At the beginning of the fifth examination, a 10 mg dose of Focalin® was administered. After 45 minutes, Participant 5B had a complete understanding of a book that demonstrated comprehension at a $7^{th}$ grade level. This level of comprehension persisted even when the Focalin® was no longer efficaciously present.

Figure 6:
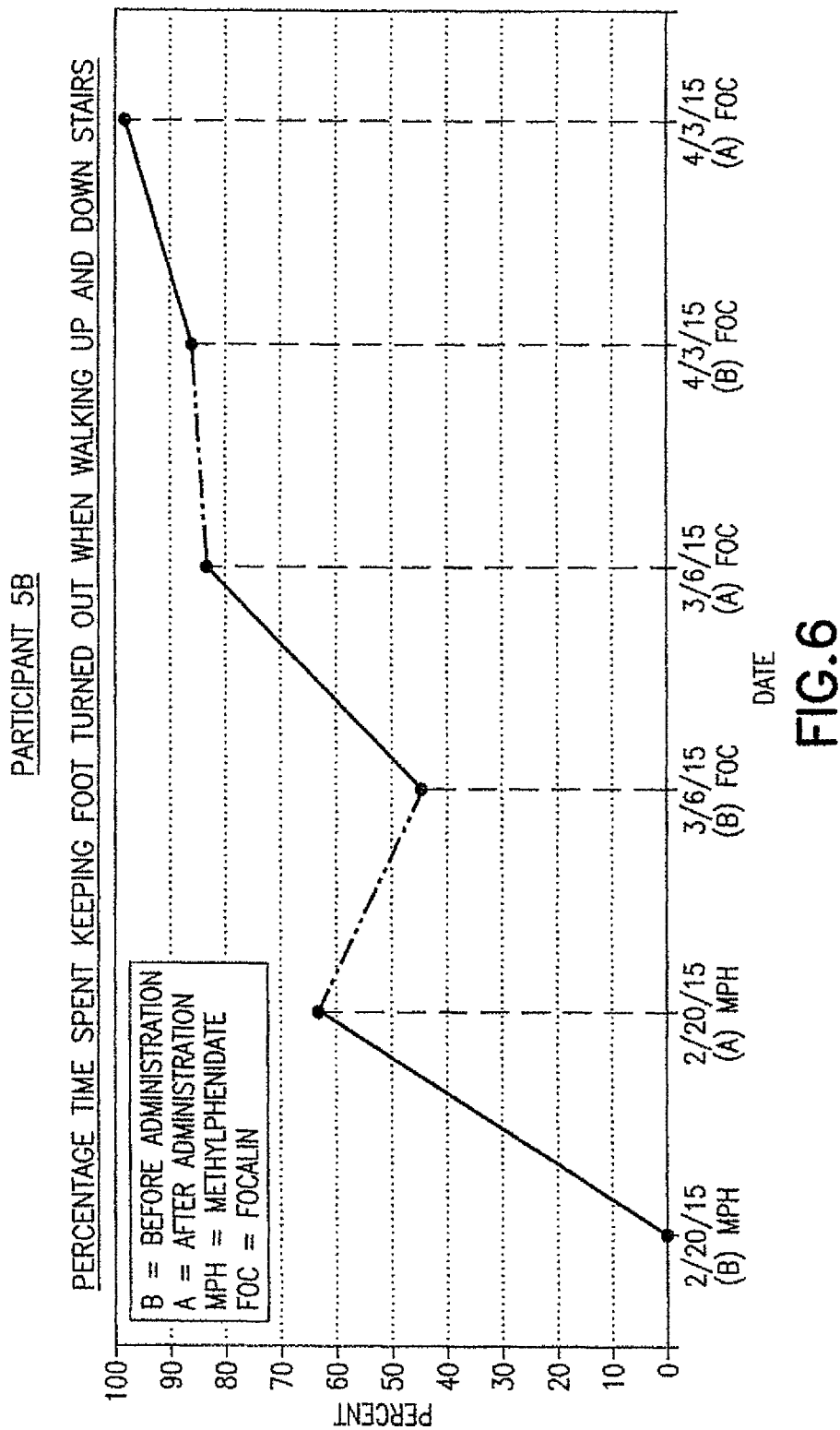
FIG. 6 is a graph of the percentage time spent keeping the foot turned out when walking up and downstairs in an initial visit/examination before and after the initial pharmaceutical intervention and in subsequent visits/examinations for Participant 5B.

Referring specifically to FIG. 6, there is shown the improvement in the percentage time keeping the foot turned outwardly as opposed to inwardly toe down, in traversing stairs for Participant 5B. The improvement is most dramatic with a Focalin® regimen in lieu of a racemic methylphenidate regimen.

The Participants 5A and 5B Examples demonstrate diminishments in both speech and gait impairments secondary to cerebral palsy. The improvements in gait speech and comprehension were particularly significant with a regimen of daily administrations of Focalin®.

Participant 6

Participant 6 is a female. At 2-3 years of age she was diagnosed with cerebral palsy.

Participant 6 had an initial visit or examination when she was 8 years old. A gait impairment, constant hand wringing and an apraxia of speech were observed. The gait impairment was a scissors gait with the ankle turning inwards and crossing over when walking.

A 5 mg MPD dose was administered to Participant 6. After 40 minutes, there was a noticeable improvement in gait. A regimen of 5 mg MPD/day was prescribed and continued for one year, at which time the dose was increased to 5 mg MPD/twice daily; once after breakfast and once after lunch. Observations for Participant 6 in subsequent visits/examinations are reported in the FIGS. 6-9, and were taken when Participant 6 was off MPD for 24 hours.

In the course of the afore-described treatment, a genetic work-up was prescribed. It was determined that Participant 6 had a polymorphism heterozygote genetic defect, namely a mutant MECP2 gene. Consequentially she was diagnosed as having Rett syndrome. Participant 6 was observed as having a motor apraxia. She exhibited constant nonspecific hand-wringing consistent with Rett syndrome.

Rett syndrome (RS) is a neurodevelopment disorder that affects girls almost exclusively. In nearly all cases of Rett syndrome, there is a mutation in the methyl CpG binding protein 2, or MECP2 gene. The symptoms are generally overlooked in the early stages. As the syndrome progresses, the child has jerkiness in limbs and gait impairments, and the child loses purposeful use their hands, characterized as constant hand washing or non-specific hand-wringing. In later stages, apraxia and particularly an apraxia of speech occur. There is no known cure for Rett syndrome, and the life expectancy at best is about 40 years, as reported in the NIH National Institute of Neurological Disorders and Stroke (NINDS) "Rett Syndrome Fact Sheet," NINDS Pub. November 2002, updated Feb. 23, 2015.

Figure 7:
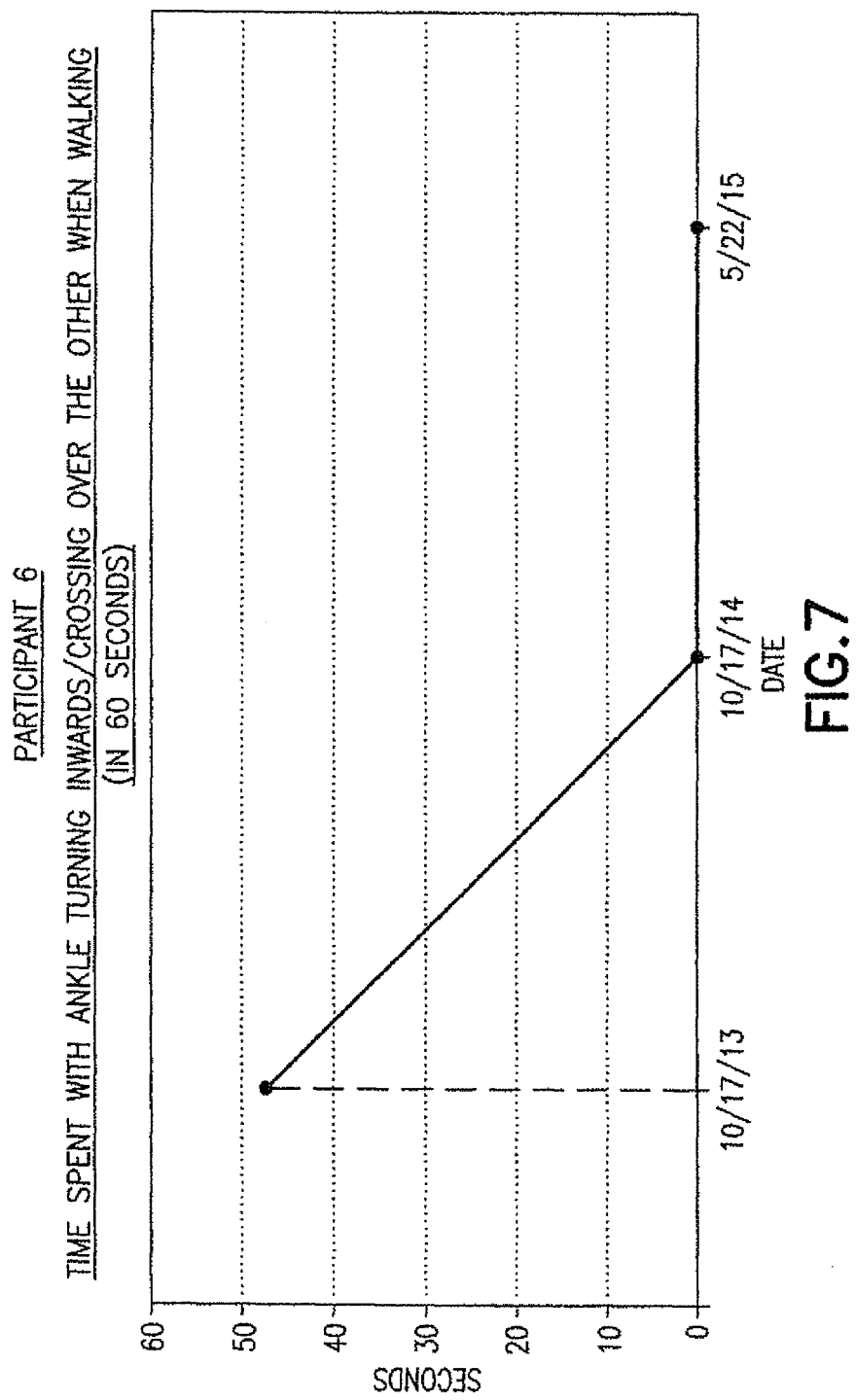
FIG. 7 is a graph of the time spent in seconds over a 60 second timeframe with the ankle turned inwards and crossing over the ankle when walking in an initial visit/examination and in subsequent visits/examinations for Participant 6.
Figure 8:
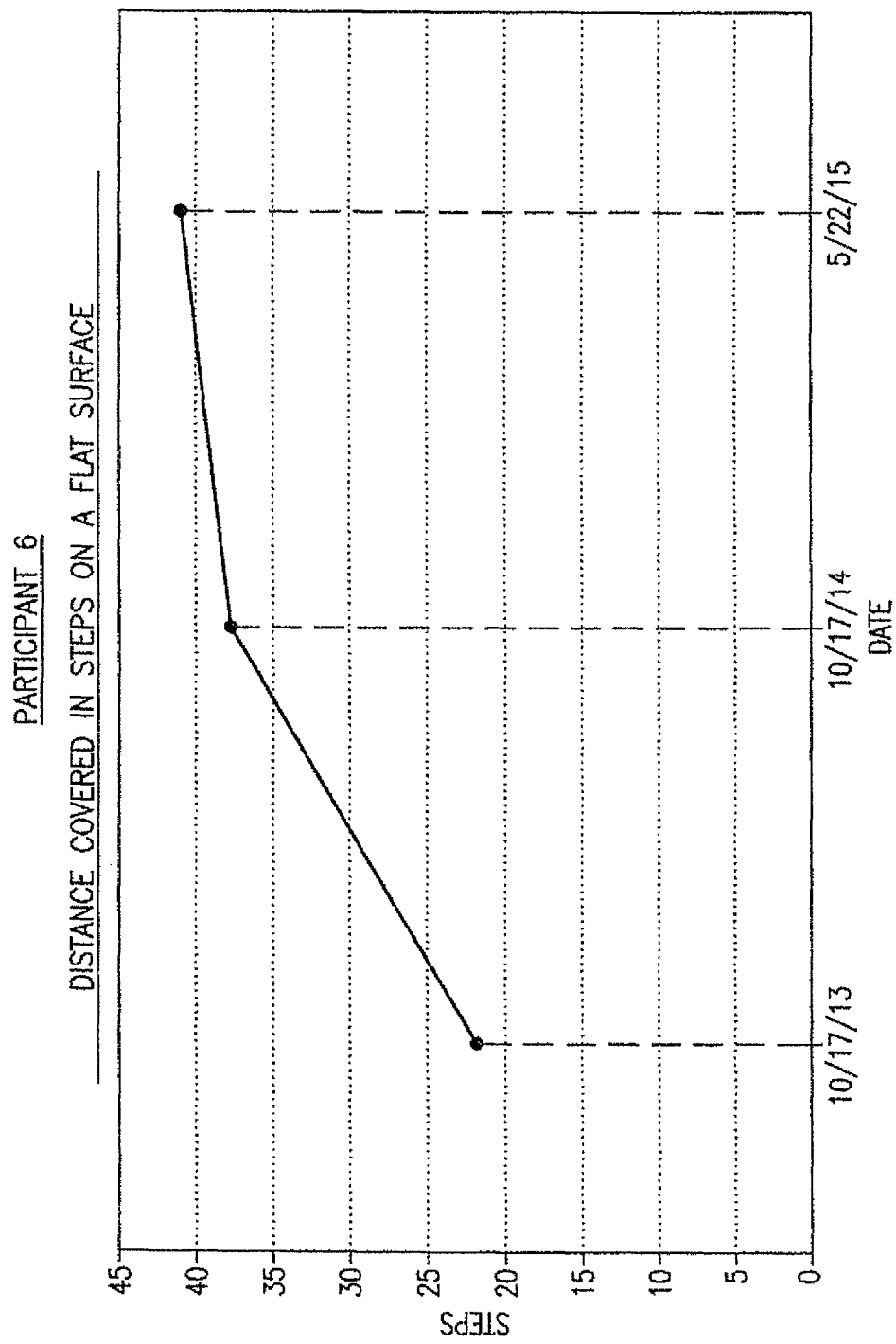
FIG. 8 is a graph of the distance covered in steps walking on a flat surface attempting to traverse a course at an initial visit/examination, and traversing the course in subsequent visits/examinations for Participant 6.
Figure 9:
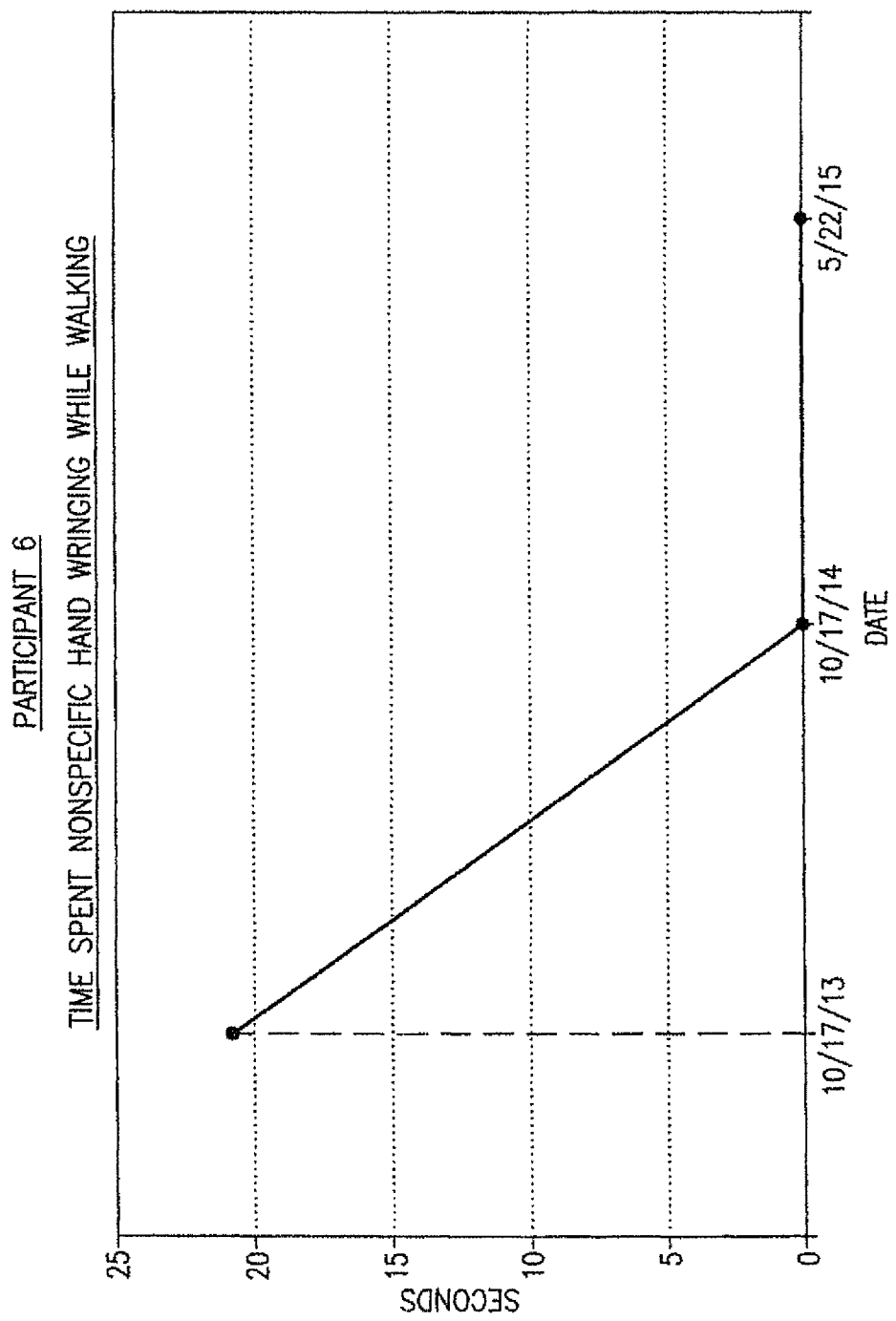
FIG. 9 is the time spent in nonspecific hand wringing while walking measured at visits/examinations during the pharmacological intervention regimen for Participant 6.

Referring specifically to FIGS. 7-9, there is shown the improvement in gait for Participant 6 in an MPD regimen over the course of a two year period. Participant 6 showed continued improvement in motor planning and execution, particularly the elimination of ankle inwards and toe down impairments. Prior to Oct. 17, 2013, Participant 6 was able to traverse only 25 feet in 60 seconds, and by May 22, 2015, Participant 6 was able to traverse 66 feet in 60 seconds. These improvements resulted from the diminishment in motor apraxia and elimination of the nonspecific hand-wringing while walking.

As demonstrated in FIG. 2 and FIGS. 7-9, the MPD course of treatment resulted in a GMFCS improvement from level number 3 to level number 1, essentially a complete diminishment of scissors gait and an essentially complete diminishment of the hand-wringing. Speech language equivalence improved dramatically over the course of treatment evidencing or diminishment of the apraxia of speech.

The Participant 6 Example demonstrates the pharmaceutical treatment of limb impairments, particularly including nonspecific hand wringing and an apraxia of speech secondary to Rett syndrome.

Participant 7

Participant 7 is a female born in 2004. The first examination was when Participant 7A was about 3 years and 4 months of age. Participant 7 had no speech. Participant 7 was diagnosed with bilateral ankle clonus, bilateral Babinski and spastic dipligea. Participant 7 was in a wheelchair. An MRI revealed brain damage consistent with cerebral palsy.

The second examination was when Participant 7 was 4½ years of age. Participant 7 remains in a wheelchair. Participant 7 was able to move her legs but not sequentially while sitting in the wheelchair. Participant 7 has leg braces.

The third examination determined that Participant 7 is not healing well because of the continued wearing of the leg braces.

The fourth examination was about three years after the third examination. Participant 7 is about 8 years of age, One month prior to the fourth examination, Participant 7 was prescribed 5 mg MPD/day. At the fourth examination, 5 mg MPD was administered. Participant 7, with assists, was able to get out of the wheelchair and had a somewhat more appropriate posture. A regimen of 5 mg MPD in the morning and in the evening was prescribed.

The fifth examination was one month after the fourth examination. It was reported by the mother and caretakers that Participant 7 was speaking more than she had in the prior month. Participant 7 shows further improvement in moving her legs in the wheelchair. The braces remain.

The sixth examination is one month after the fifth examination. Participant 7 is speaking more. The braces remain.

There is then a 2½ year hiatus during which there are no further examinations or pharmaceutical administrations pursuant to the present intervention. The examinations resumed after the 2½ year hiatus.

At the eleventh examination, the braces remain and appear to have been in place essentially during the entire 2½ year hiatus. There were brace marks on her legs as a result of the extended usage. The Participant 7 legs became weaker. The Participant 7 sedentary life style in turn caused worsened or exacerbated pain in attempts to get out of the wheelchair and stand, and then walk with a walker.

In the course of subsequent visits (examinations $12^{th}$ and $13^{th}$), in a period of about one month, Participant 7 was on a daily dosage regimen of 5 mg MPD, and then 5 mg Focalin®. Two weeks after the eleventh examination, it was agreed to remove the braces permanently. Two weeks thereafter, when Participant 7 had no longer been on MPD for 24 hours, Participant 7A exhibited the ability to stand up from the wheelchair with greater ease, to more readily walk and turn with a walker. She was more able to lift her feet and was less prone to tripping.

Figure 10:
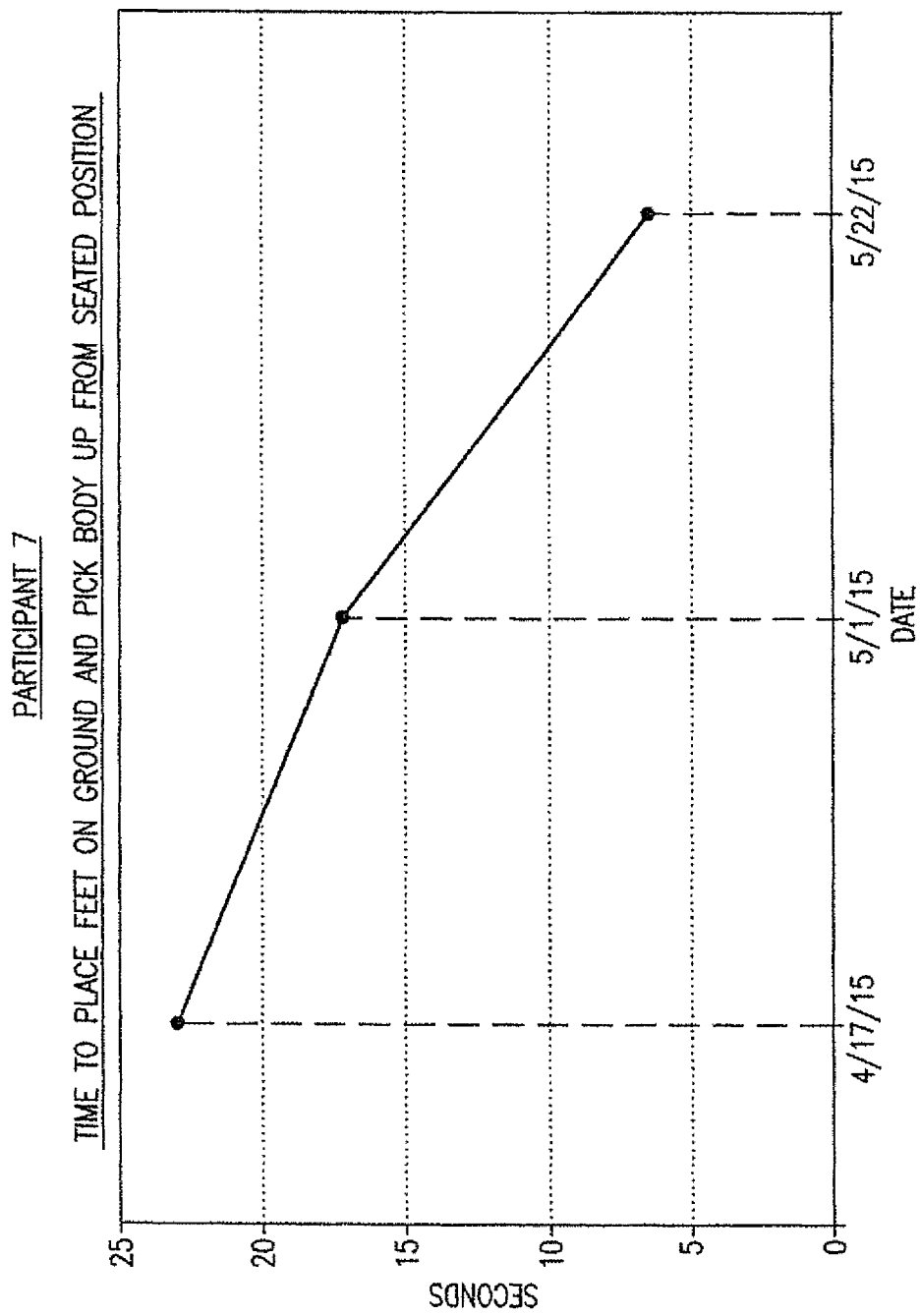
FIG. 10 is a graph of the time to place the feet on the ground and pick the body up from a seated position to standing with a walker in visits/examinations for Participant 7.

FIG. 10 shows the time spent (in seconds) unassisted in standing up from the wheelchair to a walker for Participant 7 during the 11$^{th}$ (Apr. 17, 2015), 12$^{th}$ (May 1, 2015), and 13$^{th}$ (May 22, 2015) examinations.

Figure 11:
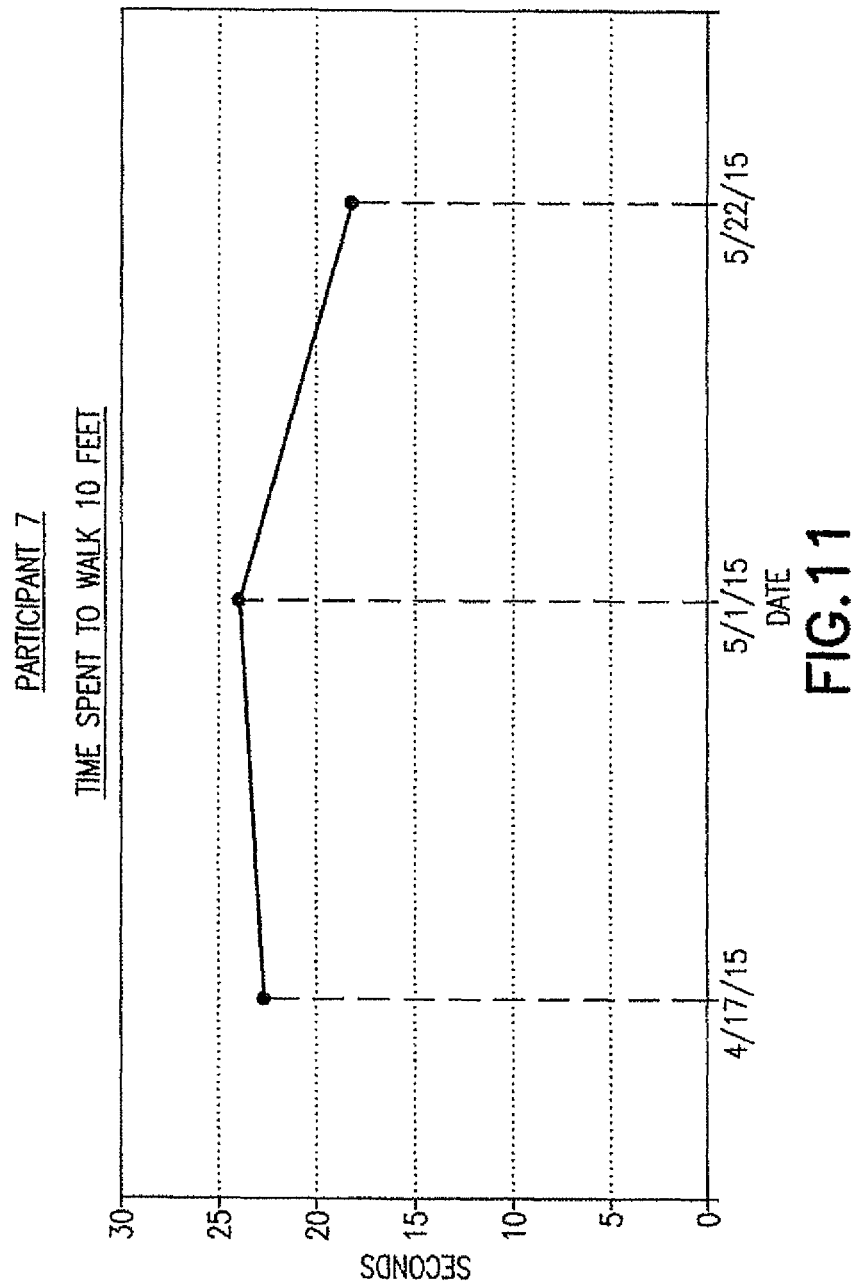
FIG. 11 is a graph of time spent to walk 10 feet during the course of the pharmacological interventions for Participant 7.

Referring specifically to FIGS. 10 and 11, Participant 7 was on a regimen of 5 mg/day Focalin® in a period from the May 1, 2015 visit/examination to the May 22, 2015 visit/examination. FIGS. 10 and 11 demonstrate the dramatic improvement with a Focalin® regimen over about a three week period.

The Participant 7 Example demonstrates that a sustained regimen of MPD and particularly Focalin, with the removal of leg braces, effected significant diminished impairment, particularly the ready ability to lift out of a wheelchair and use in a walker without tripping, Participant 7 had accordingly improved from a level 5 GFMCS to a level 3 GFMCS as shown in FIG. 2. This is a surprising and unexpected result inasmuch as generally a child at GFMCS level 5 will not improve but remain at a GFMCS level 5.

Participant 8

Participant 8 is a 39 year old male had been diagnosed with primary progressive multiple sclerosis (MS).

Participant 8 had a long history of difficulty in walking, particularly in traversing stairs, and more particularly in downwardly traversing stairs.

Participant 8 had, over the course of many years, been prescribed diverse medicaments including imuran, baclofen, as well as topical cortisone for pain after injections.

At the time of the initial examination, pursuant to the present intervention, Participant 8 was taking injections of Plegridy® (peginterferon beta-1a) every two weeks.

The initial examination, pursuant to the present intervention, revealed that the subject had a 20/200 right eye and was legally blind in the right eye. The eyes, however, moved equally and symmetrically in all directions. The subject's reflexes were 2+ everywhere with the exception of the left achilles reflex, which was absent. There was no ankle clonus. There was difficulty in balancing. There was cerebellar gait, minimally and wide based. Participant 8 had difficulty making turns, walking stairs, especially walking down stairs. The subject complained of leg spasms. The subject reported infrequent episodes of not being able to hold onto a pencil or utensil.

An MRI revealed right parietal and parafalcine lesions with involvement of the right frontal lobe and optic nerves.

Participant 8 was taken off all prior medications and prescribed a daily dose regimen of 5 mg. generic Focalin. After one month of the generic Focalin regimen, the subject was examined.

Participant 8 reported that he no longer experienced pain in his ankles. He reported walking up and down stairs with increasing speed. His stride length increased. And he is making turns on flat surfaces and stairways without hesitation.

Prior to the present intervention, Participant 8 took 15.4 seconds to go up and down a specific flight of stairs. After the present intervention, Participant 8 transversed the stairs up and down in 12.0 seconds. Prior to the present intervention, Participant 8 required 7.0 seconds to go down the flight of stairs. After the present intervention, Participant 8 required only 4.0 seconds to go down the flight of stairs.

Particularly suitable psychostimulants pursuant to the present invention include the norephinephrine-dopamine reuptake inhibitors (NDRIs) including, by way of example, methylphenidate, modafinil, armodafiml and dextro-methylphenidate, as discussed in co-pending application PCT/US2012/038312, filed May 17, 2012, and U.S. Ser. No. 14/112,065, filed Oct. 16, 2013, incorporated herein by reference thereto. Extended release, controlled release and immediate release forms methylphenidate are contemplated as useful psychostimulants. Immediate release methylphenidate is a preferred psychostimulant.

Preferred psychostimulants further include the lower alkyl phenidates, such as disclosed in Schweri et al., [$^3H$] *Threo-(±)-Methylphenidate Binding to 3,4-Dihydroxyphenylethylamine Uptake Sites in Corpus Striatum: Correlation with the Stimulant Properties of Ritalinic Acid Esters*, J. of Neurochemistry, vol. 45, no. 4, pp. 1062-70, (1985), and Portoghese et al, *Relative Hydrolytic Rates of Certain Alkyl (b) dl-α-(2-Piperidyl)-phenylacetrates*, J. Pharmaceutical Science, vol. 50, no. 6, pp. 494-51, and U.S. Pat. No. 6,528,530, issued Mar. 4, 2003 to Zeitlin, et al. Preferred psychostimulants also include the nonlinear lower alkyl phenidates, namely isopropyl, isobutyl, d-isoproyl, d-isobutyl, d-threo-isopropyl, d-threo, isopropyl, sec-butyl and t-butyl.

Alkyl phenidates, racemic mixtures and isolated individual isomers are known in the art, as disclosed in U.S. Pat. No. 2,507,631, issued May 16, 1950 to Hartmann et al, U.S. Pat. No. 2,157,880, issued Oct. 25, 1960 to Rometsch, and U.S. Pat. No. 5,908,850 issued Jun. 1, 1999 to Zeitlin et al; which references are incorporated herein in their entireties by reference thereto. Alkyl phenidates are commercially available, including by way of specific examples, dextro-threo-methylphenidate (Focalin®) and isopropylphenidate.

Without wishing to be bound by any theory or mechanism, it is believed that the nonlinear lower alkyl phenidates provide hindrance to unwarranted esterfication which in turn causes adverse side effects, particularly adverse in children.

In the art related to the treatment of hyperactivity in children, particularly including ADD and ADHD, it is established practice to administer methylphenidate. Psychosocial behavioral disorders such as lack of attentiveness and verbal regression are improved with the administration of methylphenidate, as disclosed in U.S. Pat. No. 6,121,261, issued Sep. 19, 2006 to Glatt et al; and Creager et al., Journal of Speech and Hearing Research, 623-628 (1967). Methylphenidate is administered daily to children suffering psychobehavioral and neuropsychological disorders. The behavioral improvement is short lived, and lasts, at most, several hours after administration of the methylphenidate. Unless such daily dosages are maintained, the subject reverts to his or her attention deficits and hyperactivity.

One further most preferred methylphenidate is an extended release powder in aqueous suspension as disclosed in US 2013/0004571 A1, published Jan. 3, 2013 to Metha et al., which is incorporated herein in its entirety by reference thereto. The aqueous suspension is particularly administrable to children with infantile cerebral palsy.

Gaboxadol®, also known as 4.5.6.7-tetrahydroisoxazolor (5,4-c)pyridine-3-ol (THIP), and its analogs are contemplated to treat Angelman syndrome and Fragile-X syndrome (FXS). The present invention contemplates a psychostimulant, particularly including a methylphenidate, in combination with THIP or an analog of THIP to treat speech, gait or limb impairments secondary to AS or to a THIP regimen resultant impairment.

Thalidomide and its analogs are contemplated to treat multiple sclerosis (MS). The present invention contemplates a psychostimulant, particularly a methylphenidate, in combination with thalidomide or an analog to treat speech, gait and limb impairments secondary to MS or thalidomide regimen resultant.

The foregoing Examples demonstrate that pre-frontal cortex processing disorders diseases or disorders having secondary speech, gait and limb impairments.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the subject being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A pharmaceutical intervention for a speech, gait or limb impairment secondary to multiple sclerosis in a subject in need of such intervention, said pharmaceutical intervention comprises:
   a psychostimulant having mood-elevating properties or antidepressant activity, said psychostimulant comprises methylphenidate;
   whereby the speech, gait or limb impairment is diminished.

2. The pharmaceutical intervention of claim 1, said psychostimulant comprises dextro-threo-methylphenidate.

3. The pharmaceutical intervention of claim 1, said methylphenidate comprises a non linear lower alkyl phenidate.

4. The pharmaceutical intervention of claim 3, wherein the non linear lower alkyl phenidate comprises isopropylphenidate.

5. A method for treating a speech, gait or limb impairment secondary to multiple sclerosis in a subject in need of such treatment, said method comprises:
   administering a therapeutically effective dose of a psychostimulant having mood-altering or anti-depressant activity to the subject, said psychostimulant comprises and NDRI;
   whereby the impairment is diminished.

6. The method of claim 5, wherein the NDRI comprises a methylphenidate.

7. The method of claim 6, wherein the methylphenidate comprises dextro-threo-methylphenidate.

8. In combination:
   a first pharmaceutical intervention, said first pharmaceutical intervention treating a pre-frontal cortex processing disorder in a subject in need of such treatment, said disorder comprises genetically acquired multiple sclerosis (MS), and wherein there is a gait or limb impairment secondary to the disorder; and
   a second pharmaceutical intervention treating the impairment, said second pharmaceutical intervention comprises a psychostimulant having mood-elevating properties or antidepressant activity, said second pharmaceutical intervention comprises a methylphenidate;
   whereby the impairment is diminished with treatment of the disorder.

9. The combination of claim 8, wherein the impairment is manifested in childhood.

10. The combination of claim 8, wherein the methylphenidate comprises dextro-threo-methylphenidate.

11. The combination of claim 10, wherein the impairment comprises a gait impairment, and wherein the diminishment in the gait impairment persists when the dextro-threo-methylphenidate is no longer efficaciously present in the subject.

12. The combination of claim 8, wherein the methylphenidate consists essentially of dextro-threo-methylphenidate.

13. The pharmaceutical intervention of claim 1, wherein the subject is a child.

14. The pharmaceutical intervention of claim 1, wherein the disorder is genetically acquired.

15. The pharmaceutical intervention of claim 1, wherein the disorder is acquired genetically, in utero, during birth or in infancy, and the impairment is later manifested in the subject.

16. The method of claim 5, wherein the subject is a child.

17. The method of claim 5, wherein the disorder is genetically acquired.

18. The method of claim 5, wherein the disorder is acquired genetically, in utero, during birth or in infancy, and the impairment is later manifested in the subject.

19. The combination of claim 8, wherein the subject is a child.

20. The combination of claim 8, wherein the disorder is genetically acquired.

21. The combination of claim 8, wherein the disorder is acquired genetically, in utero, during birth or in infancy, and the impairment is later manifested in the subject.

* * * * *